(12) United States Patent
Hoang et al.

(10) Patent No.: US 7,064,096 B1
(45) Date of Patent: Jun. 20, 2006

(54) DUAL CATALYST ON A SINGLE SUPPORT

(75) Inventors: Peter Phung Minh Hoang, Calgary (CA); Cliff Robert Baar, Calgary (CA); Peter Zoricak, Calgary (CA); Gail Baxter, Calgary (CA)

(73) Assignee: Nova Chemicals (International) SA (CH)

( * ) Notice: Subject to any disclaimer, the term of this patent is extended or adjusted under 35 U.S.C. 154(b) by 23 days.

(21) Appl. No.: 11/006,436

(22) Filed: Dec. 7, 2004

(51) Int. Cl.
*B01J 31/38* (2006.01)
*C08F 4/76* (2006.01)
*C08F 4/44* (2006.01)

(52) U.S. Cl. .................. 502/103; 502/129; 526/120; 526/118; 526/119; 526/121; 526/172; 526/161; 526/134

(58) Field of Classification Search ............ 526/120, 526/118, 119, 121, 172, 161, 134; 502/128, 502/103, 129
See application file for complete search history.

(56) References Cited

U.S. PATENT DOCUMENTS

| | | | |
|---|---|---|---|
| 4,530,914 A | 7/1985 | Ewen et al. | 502/113 |
| 5,434,116 A | 7/1995 | Sone et al. | 502/103 |
| 5,554,775 A | 9/1996 | Krishnamurti et al. | 556/7 |
| 5,637,659 A | 6/1997 | Krishnamurti et al. | 526/133 |
| 6,235,672 B1 * | 5/2001 | McKay et al. | 502/155 |
| 6,277,931 B1 * | 8/2001 | Jaber et al. | 526/65 |
| 6,309,997 B1 | 10/2001 | Fujita et al. | 502/167 |
| 6,486,273 B1 * | 11/2002 | McKay et al. | 526/113 |
| 2002/0045711 A1 | 4/2002 | Backman et al. | 525/240 |
| 2002/0077431 A1 * | 6/2002 | Whiteker | 526/113 |

OTHER PUBLICATIONS

A. Noshay and F.J. Karol, Chemical Activation of Silica Supports, for Chromocene-Based Polyethylene Catalysts, pp. 396–416, Transition Metal Catalyzed Polymerizations, 1989.

J.B. Peri and A.L. Hensley, Jr., The Surface Structure of Silica Gel, The Journal of Physical Chemistry, vol. 72, No. 8, Aug. 1968, pp. 2926–2933.

Corwin Hansch, A. Leo, and R.W. Taft, A Survey of Hammett Substituent Constants and Resonance and Field Parameters, Chem. Rev. 1991, 91, 165–195.

* cited by examiner

Primary Examiner—David W. Wu
Assistant Examiner—Rip A. Lee
(74) Attorney, Agent, or Firm—Kenneth H. Johnson

(57) ABSTRACT

Bimodal polyolefins having a reverse or partial reversed comonomer incorporation may be prepared in the presence of a dual catalyst on the same support wherein each catalyst has a different response to temperature, ethylene partial pressures, partial pressure of non-polymerizable hydrocarbons present in the reaction mixture and hydrogen partial pressure.

27 Claims, 3 Drawing Sheets

DUAL CATALYST ON A SINGLE SUPPORT

FIELD OF THE INVENTION

The present invention relates to a dual catalyst system on the same support.

BACKGROUND OF THE INVENTION

The original single site catalysts of the mid 1980's, such as metallocene catalysts, produced resin having a narrow polydispersity (Mw/Mn) typically in the range from about 2.5 to 3.5. Early on it was recognized that either blending such resins or the use of different metallocene catalysts in the same reactor could produce bimodal resins, each component having a narrow polydispersity and the blend having a broader polydispersity. It was felt such resins would provide a good balance of processability and physical properties such as resin toughness. There are an increasing number of patents and applications in this field.

U.S. Pat. No. 4,530,914 issued Jul. 23, 1985 to Ewen et al., assigned to EXXON Research & Engineering Co. teaches the use in the same reactor of two metallocene catalysts each having different propagation and termination rate constants for ethylene polymerizations. The catalyst combination taught in the patent is not the same as that contemplated by the present invention.

There are a number of patents wherein a bimodal resin is produced having a controlled molecular weight distribution by using different single site catalysts such as metallocene in two or more tandem reactors. United States patent application 2002/0045711 in the name of Backman et al., published Apr. 18, 2002 is illustrative of this type of art. The reference teaches away from the present invention in that the present invention contemplates the use of a single reactor, not tandem reactors.

U.S. Pat. No. 6,309,997 issued Oct. 30, 2001 teaches an olefin polymerization catalyst using a phenoxide (preferably a salicylaldimine) ligand for use in the polymerization of olefins. The patent does not teach the use of mixed catalysts systems for bimodal resins nor does it teach process control to adjust the polymer characteristics such as bimodality and comonomer incorporation.

United States patent application 2002/0077431 published Jun. 20, 2002 in the name of Whiteker discloses a process for the polymerization and oligomerization of olefins in the presence of a mixed catalyst system in a single reactor. The catalyst system as disclosed comprises a first component similar to the first component in the catalyst system of the present invention except that at least one of substituents $R^3$, $R^4$, $R^5$, $R^8$, $R^9$ and $R^{10}$ must have a Hammett $\sigma_p$ value (Hansch et al., Chem. Rev. 1991,91,165) greater than 0.2 (i.e. at least one of these substituents needs to be a sufficiently electron withdrawing group (e.g. $CF_3$, Br, etc.)). In the catalysts and process according to the present invention none of $R^3$, $R^4$, $R^5$, $R^8$, $R^9$ and $R^{10}$ have a Hammett ($\sigma_p$) value of greater than 0.2. Further the reference fails to teach or suggest the molecular weight distribution of the components in the resulting polymer may be altered or controlled by altering or controlling the reaction conditions.

The present invention seeks to provide novel useful catalysts suitable for the polymerization of bimodal polyolefins (e.g. polyethylene) having reverse or partial reverse comonomer incorporation.

SUMMARY OF THE INVENTION

The present invention provides a dual catalyst system suitable for producing a bimodal resin having at least one higher molecular weight fraction having a greater comonomer incorporation than that of a lower molecular weight fraction wherein:

(i) the first component of which comprises a catalyst of the formula:

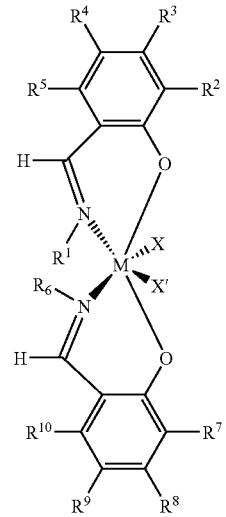

wherein M is a transition metal, preferably a group 4 transition metal, most preferably selected from the group consisting of Ti, Hf and Zr; $R^1$ and $R^6$ are independently selected from the group consisting of a hydrogen atom, alkyl radicals having up to 15, preferably from 1 to 8, most preferably from 1 to 6 carbon atoms, aryl radicals having up to 25, preferably from 6 to 18, most preferably from 6 to 12 carbon atoms, alkoxy radicals having up to 15, preferably from 1 to 8, most preferably from 1 to 6 carbon atoms, and amido radicals which are unsubstituted or substituted by up to two alkyl radicals containing up to 15, preferably from 1 to 8, most preferably from 1 to 6 carbon atoms, $R^2$ and $R^7$ are independently selected from the group consisting of alkyl radicals having up to 15, preferably from 1 to 8, most preferably from 1 to 6 carbon atoms, aryl radicals having up to 25, preferably from 6 to 18, most preferably from 6 to 12 carbon atoms and silyl radicals of the formula $Si(R^{11})_3$ wherein each $R^{11}$ is independently selected from the group consisting of alkyl radicals having up to 15, preferably from 1 to 8, most preferably from 1 to 6 carbon atoms, and aryl radicals having up to 25, preferably from 6 to 18, most preferably from 6 to 12 carbon atoms; $R^3$, $R^4$, $R^5$, $R^8$, $R^9$ and $R^{10}$ are independently selected from the group consisting of a hydrogen atom, a heteroatom containing group having up to 20, preferably from 1 to 18, most preferably from 1 to 12 carbon atoms, and a hydrocarbon group containing up to 25 carbon atoms, provided that none of these groups has a Hammett $\sigma_p$ value greater than 0.20; X and X' are activatable groups;

(ii) the second component of which comprises a catalyst of the formula:

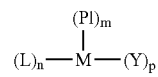

wherein M is a group 4 metal; Pl is a phosphinimine ligand; L is a monoanionic ligand selected from the group consisting of a cyclopentadienyl-type ligand or a bulky heteroatom ligand; Y is an activatable ligand; m is 1 or 2; n is 0 or 1; and p is an integer and the sum of m+n+p equals the valence state of M.

The present invention further provides a gas phase process for controlling the ratio of high molecular weight polymer to low molecular weight polymer in a single reactor at a temperature from 50 to 120° C. of a reaction mixture comprising one or more of hydrogen, nitrogen, $C_{1-7}$ non polymerizable hydrocarbons, and $C_{2-8}$ olefins polymerized in the presence of a dual catalyst as described above, which comprises one or more steps selected from the group consisting of:

(a) altering the temperature of the reaction by at least 2° C. within the range from 50 to 120° C.;

(b) altering the partial pressure of the hydrogen component of the reaction mixture by at least 0.02 psi (0.138 KPa);

(c) altering the partial pressure of one or more of the $C_{2-8}$ olefins in the reaction mixture by not less than 10 psi (68.94 KPa); and (d) altering the amount of non polymerizable hydrocarbon in the reaction mixture by not less than 0.5 mole %.

In a slurry process (a) through (c) would be used to control the polymer characteristics.

DETAILED DESCRIPTION

Figure 1:
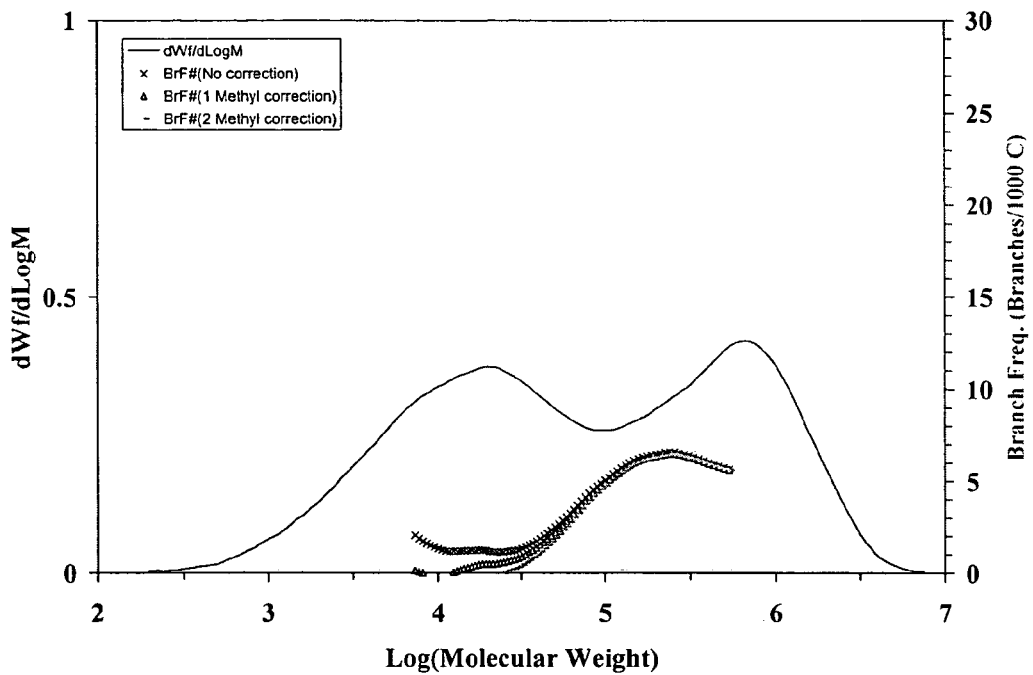
FIG. 1 is a GPC-FTIR profile of the resin produced in Example 1.

As used in this specification the following words or phrases have the following meanings.

Polydispersity is the ratio of the weight average molecular weight (as determined by GPC) to the number average molecular weight (as determined by GPC) (i.e. Mw/Mn) of any component in the blend or the blend per se.

Cyclopentadienyl refers to a 5-member carbon ring having delocalized bonding within the ring and typically being bound to the active catalyst site, generally a group 4 metal (M) through $\eta^5$-bonds.

The phrase mixed catalyst or dual catalyst or catalyst system on a single support means that both components are on the same support (e.g. the catalyst components are deposited (either sequentially or concurrently) on the same support particles). It does not mean that the catalyst is a blend of two or more catalysts each of which happen to be on the same type of or a similar type of support.

The phrase reverse or partial reverse comonomer incorporation means that on deconvolution of the GPC-FTIR (or TREF) data (profiles) (typically using molecular weight distribution segments of not less than 10,000) there is one or more higher molecular component having a higher comonomer incorporation than the comonomer incorporation in one or more lower molecular segments. If the comonomer incorporation is rising with molecular weight the distribution would be reverse. However the comonomer incorporation may rise with increasing molecular weight then decline in which case the comonomer distribution would be partially reverse (or partially regular).

The gas phase polymerization of olefins and particularly alpha-olefins has been known for at least about 30 years. Generally a gaseous mixture comprising from 0 to 15 mole % of hydrogen, from 0 to 30 mole % of one or more $C_{3-8}$ alpha-olefins, from 15 to 100 mole % of ethylene, and from 0 to 75 mole % of non-polymerizable gas at a temperature from 50° C. to 120° C., preferably from 60° C. to 120° C., most preferably from 75° C. to about 110° C., and at pressures typically not exceeding 3,500 kPa (about 500 psi), preferably not greater than 2,400 kPa (about 350 psi) are polymerized in the presence of a mixed catalyst system on a single support in a single rector.

The slurry phase polymerization of olefins has been known for about 30 years. Generally a mixture comprising from 0 to 15 mole % of hydrogen, from 0 to 30 mole % of one or more $C_{3-8}$ alpha olefins, from 15 to 100 mole % of ethylene, and from 0 to 75 mole % of an inert gas is dissolved in an inert hydrocarbyl diluent such as $C_{4-10}$ hydrocabons and $C_{6-10}$ aryl or arylalkyl hydrocarbons. The mixture is then polymerized at a temperature from 50° C. to 120° C., preferably from 60° C. to 120° C., most preferably from 70° C. to about 110° C., and at pressures typically not exceeding 3,500 kPa (about 500 psi), preferably not greater than 2,400 kPa (about 350 psi) is polymerized in the presence of a mixed catalyst system on a single support in a single rector.

Suitable olefin monomers may be ethylene and $C_{3-20}$ mono- and di-olefins. Preferred monomers include ethylene and $C_{3-8}$ alpha olefins which are unsubstituted or substituted by up to two $C_{1-6}$ alkyl radicals. Illustrative non-limiting examples of such alpha olefins are one or more of propylene, 1-butene, 1-pentene, 1-hexene and 1-octene.

The polyethylene polymers which may be prepared in accordance with the present invention typically comprise not less than 60, preferably not less than 70, most preferably not less than 80 weight % of ethylene with the balance being one or more $C_{3-8}$ alpha olefins, preferably selected from the group consisting of 1-butene, 1-hexene and 1-octene.

The polymers prepared in accordance with the present invention have a bimodal or multimodal molecular weight distribution. Overall, the weight average molecular weight (Mw) will preferably be greater than about 50,000 ranging up to $10^7$, preferably $10^5$ to $10^7$. There will be a lower molecular weight component seen as a peak or shoulder on a GPC analysis and there will be one or more higher molecular weight components also seen as a separate peak or shoulder on a GPC analysis. Generally the lower molecular weight component will be present in an amount from 20 to 80, preferably from 30 to 70, most preferably from 35 to 65 weight % of the total bimodal resin. The high molecular component may be present in amounts from 80 to 20, preferably 70 to 30, most preferably from about 65 to 35 weight % of the total polymer.

The low molecular weight polyethylene may have a weight average molecular weight greater than 5,000, typically from 10,000 to 140,000, preferably from about 15,000 to about 100,000, most preferably from about 20,000 to 100,000 as estimated by deconvolution of a GPC curve. The low molecular weight polyethylene may have a polydispersity (Mw/Mn) greater than about 3, typically from 3 to 15, preferably from about 5 to 12.

The high molecular weight polyethylene may have a weight average molecular a weight greater than 200,000, typically from 250,000 to 600,000 as determined by deconvolution of a GPC curve. The high molecular weight polyethylene may have a polydispersity (Mw/Mn) less than about 10, typically from 2 to 8.

The catalyst system of the present invention may be supported on a refractory support or an organic support (including polymeric support). That is both catalyst components are supported on the same refractory support or an organic support (e.g. polymeric). Some refractories include silica which may be treated to reduce surface hydroxyl groups and alumina. The support or carrier may be a spray-dried silica. Generally the support will have an average particle size from about 0.1 to about 1000, preferably from about 10 to 150 microns. The support typically will have a surface area of at least about 100 m²/g, preferably from about 150 to 1,500 m²/g. The pore volume of the support should be at least 0.2, preferably from about 0.3 to 5.0 ml/g.

Generally the refractory or inorganic support may be heated at a temperature of at least 200° C. for up to 24 hours, typically at a temperature from 500° C. to 800° C. for about 2 to 20, preferably 4 to 10 hours. The resulting support will be free of adsorbed water and should have a surface hydroxyl content from about 0.1 to 5 mmol/g of support, preferably from 0.5 to 3 mmol/g.

A silica suitable for use in the present invention has a high surface area and is amorphous. For example, commercially available silicas are marketed under the trademark of Sylopol® 958 and 955 by the Davison Catalysts, a Division of W. R. Grace and Company and ES-70W by Ineos Silica.

The amount of the hydroxyl groups in silica may be determined according to the method disclosed by J. B. Peri and A. L. Hensley, Jr., in *J. Phys. Chem.*, 72 (8), 2926, 1968, the entire contents of which are incorporated herein by reference.

While heating is the most preferred means of removing OH groups inherently present in many carriers, such as silica, the OH groups may also be removed by other removal means, such as chemical means. For example, a desired proportion of OH groups may be reacted with a suitable chemical agent, such as a hydroxyl reactive aluminum compound (e.g. triethyl aluminum) or a silane compound. This method of treatment has been disclosed in the literature and two relevant examples are: U.S. Pat. No. 4,719,193 to Levine in 1988 and by Noshay A. and Karol F. J. in *Transition Metal Catalyzed Polymerizations*, Ed. R. Quirk, 396, 1989. For example, the support may be treated with an aluminum compound of the formula $Al((O)_aR^1)_bX_{3-b}$ wherein a is either 0 or 1, b is an integer from 1 to 3, $R^1$ is a $C_{1-8}$ alkyl radical, and X is a chlorine atom. The amount of aluminum compound is such that the amount of aluminum on the support prior to adding the remaining catalyst components will be from about 0 to 2.5 weight %, preferably from 0 to 2.0 weight % based on the weight of the support.

The polymeric support may be cross linked polystyrene containing up to about 20 weight % preferably less than 10 weight %, most preferably from about 2 to 8 weight % of a cross linking agent such as divinyl benzene.

In accordance with the present invention the two catalysts are deposited on the same support (i.e. both catalysts must be on each particle of support). The catalysts may be used in a molar ratio of the active transition metal of the first catalyst to the second catalyst from 80:20 to 20:80 preferably from 60:40 to 40:60. While the present invention is directed to both catalysts being on the same support, it is expected it would be possible to achieve similar results by blending two catalysts on similar or comparable supports to provide the same ratio of catalysts.

In accordance with the present invention the first catalyst comprises a catalyst of the formula I:

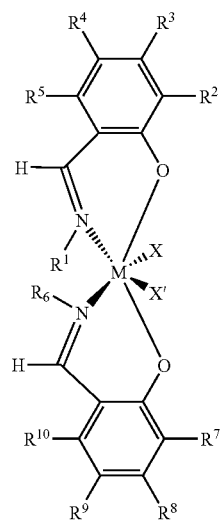

wherein M is a Group IV transition metal preferably Ti or Zr; $R^1$ and $R^6$ are independently selected from the group consisting of a hydrogen atom, alkyl radicals having up to 15, preferably from 1 to 8, most preferably from 1 to 6 carbon atoms, aryl radicals having up to 25, preferably from 6 to 18, most preferably from 6 to 12 carbon atoms, alkoxy radicals having up to 15, preferably from 1 to 8, most preferably from 1 to 6 carbon atoms, and amido radicals which are unsubstituted or substituted by up to two alkyl radicals containing up to 15, preferably from 1 to 8, most preferably from 1 to 6 carbon atoms, $R^2$ and $R^7$ are independently selected from the group consisting of alkyl radicals having up to 15, preferably from 1 to 8, most preferably from 1 to 6 carbon atoms, aryl radicals having up to 25, preferably from 6 to 18, most preferably from 6 to 12 carbon atoms and silyl radicals of the formula $Si(R^{11})_3$ wherein each $R^{11}$ is independently selected from the group consisting of alkyl radicals having up to 15, preferably from 1 to 8, most preferably from 1 to 6 carbon atoms, and aryl radicals having up to 25, preferably from 6 to 18, most preferably from 6 to 12 carbon atoms; $R^3$, $R^4$, $R^5$, $R^8$, $R^9$ and $R^{10}$ are independently selected from the group consisting of a hydrogen atom, a heteroatom containing group having up to 20, preferably from 1 to 18, most preferably from 1 to 12 carbon atoms, and a hydrocarbon group containing up to 25 carbon atoms, provided that none of these groups has a Hammett $\sigma_p$ value greater than 0.20; X and X' are activatable or leaving groups.

In the first catalyst (first component) preferably $R^3$, $R^4$, $R^5$, $R^8$, $R^9$ and $R^{10}$ are selected from the group consisting of a hydrogen atom and $C_{1-15}$, preferably $C_{1-8}$, most preferably $C_{1-6}$ alkoxy radicals. Preferably $R^3$, $R^5$, $R^8$ and $R^{10}$ are hydrogen.

As noted above none of $R^3$, $R^4$, $R^5$, $R^8$, $R^9$ and $R^{10}$ has a Hammett $\sigma_p$ value (Hansch et al., Chem Rev. 1991, 91, 165) greater than 0.2.

Activatable or leaving groups are well known to those skilled in the art. Generally, they may be selected from the group consisting of a halogen atom, alkyl radicals having up to 15, preferably from 1 to 8, most preferably from 1 to 6 carbon atoms, aryl radicals having up to 25, preferably from 6 to 18, most preferably from 6 to 12 carbon atoms, alkoxy radicals having up to 15, preferably from 1 to 8, most preferably from 1 to 6 carbon atoms, amido radicals which are unsubstituted or substituted by up to two alkyl radicals containing up to 15, preferably from 1 to 8, most preferably from 1 to 6 carbon atoms, and phenoxy radicals having up to 18, preferably from 6 to 12 carbon atoms.

The synthesis of desired ligands of the first catalyst can be accomplished by reaction of salicylaldehydes with amines. Preparation of the requisite salicylaldehydes can be accomplished using standard synthetic techniques.

Metallation of the ligands can be accomplished by reaction with basic reagents such as $Zr(CH_2Ph)_4$. Reaction of the ligands with $Zr(CH_2Ph)_4$ occurs with elimination of toluene. Alternately, ligands can be deprotonated with reagents such as BuLi, KH or Na metal and then reacted with metal halides, such as $ZrCl_4$.

The second component of the catalyst system (second catalyst) is a catalyst of the formula II:

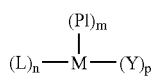

wherein M is a group 4 metal; Pl is a phosphinimine ligand; L is a monoanionic ligand selected from the group consisting of a cyclopentadienyl-type ligand or a bulky heteroatom ligand; Y is an activatable ligand; m is 1 or 2; n is 0 or 1; and p is an integer and the sum of m+n+p equals the valence state of M.

The preferred metals (M) are from Group 4 (especially titanium, hafnium or zirconium) with titanium being most preferred.

The phosphinimine ligand is defined by the formula:

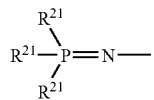

wherein each $R^{21}$ is independently selected from the group consisting of a hydrogen atom; a halogen atom; $C_{1-20}$, preferably $C_{1-10}$ hydrocarbyl radicals which are unsubstituted by or further substituted by a halogen atom; a $C_{1-8}$ alkoxy radical; a $C_{6-10}$ aryl or aryloxy radical; an amido radical; a silyl radical of the formula:

wherein each $R^{22}$ is independently selected from the group consisting of hydrogen, a $C_{1-8}$ alkyl or alkoxy radical, and $C_{6-10}$ aryl or aryloxy radicals; and a germanyl radical of the formula:

wherein $R^{22}$ is as defined above.

In the second catalyst preferably Y is selected from the group consisting of a hydrogen atom; a halogen atom, a $C_{1-10}$ hydrocarbyl radical; a $C_{1-10}$ alkoxy radical; a $C_{5-10}$ aryl oxide radical; each of which said hydrocarbyl, alkoxy, and aryl oxide radicals may be unsubstituted by or further substituted by one or more substituents selected from the group consisting of a halogen atom; a $C_{1-8}$ alkyl radical; a $C_{1-8}$ alkoxy radical; a $C_{6-10}$ aryl or aryloxy radical; an amido radical which is unsubstituted or substituted by up to two $C_{1-8}$ alkyl radicals; and a phosphido radical which is unsubstituted or substituted by up to two $C_{1-8}$ alkyl radicals. Most preferably Y is selected from the group consisting of a hydrogen atom, a chlorine atom and a $C_{1-4}$ alkyl radical.

In the second component of the catalyst system (second catalyst) L is a monoanionic ligand selected from the group consisting of a cyclopentadienyl-type ligand or a bulky heteroatom ligand, preferably L is a cyclopentadienyl type ligand.

As used herein, the term "bulky heteroatom ligand" refers to a ligand which contains at least one heteroatom selected from the group consisting of boron, nitrogen, oxygen, phosphorus or sulfur. The heteroligand may be sigma or pi-bonded to the metal. Exemplary heteroligands include ketimide ligands, silicone-containing heteroligands, amido ligands, alkoxy ligands, boron heterocyclic ligands (e.g. borabenzene ligands) and phosphole ligands, as all described below.

As used herein, the term "ketimide ligand" refers to a ligand which:

(a) is bonded to the transition metal via a metal-nitrogen atom bond;

(b) has a single substituent on the nitrogen atom, (where this single substituent is a carbon atom which is doubly bonded to the N atom); and (c) has two substituents Sub 1 and Sub 2 (described below) which are bonded to the carbon atom.

Conditions a, b and c are illustrated below:

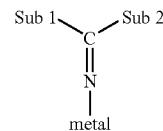

The substituents "Sub 1" and "Sub 2" may be the same or different and can be bonded to each other to form a ring. Exemplary substituents include hydrocarbyls having from 1 to 20 carbon atoms, silyl groups, amido groups and phosphido groups. For reasons of cost and convenience it is preferred that these substituents both be hydrocarbyl radicals, especially simple alkyl radicals (e.g. $C_{1-6}$, preferably $C_{1-4}$) and most preferably tertiary butyl.

Silicon containing heteroligands are defined by the formula:

wherein the - denotes a bond to the transition metal and μ is sulfur or oxygen.

The substituents on the Si atom, namely $R_x$, $R_y$ and $R_z$ are required in order to satisfy the bonding orbital of the Si atom. The use of any particular substituent $R_x$, $R_y$ or $R_z$ is not especially important to the success of this invention. It is preferred that each of $R_x$, $R_y$ and $R_z$ is a $C_{1-2}$ hydrocarbyl group (i.e. methyl or ethyl) simply because such materials are readily synthesized from commercially available materials.

The term "amido" is meant to convey its broad, conventional meaning. Thus, these ligands are characterized by (a) a metal-nitrogen bond; and (b) the presence of two substituents, which are typically simple alkyl ($C_{1-6}$, preferably $C_{1-4}$) or silyl groups on the nitrogen atom.

The terms "alkoxy" and "aryloxy" are also intended to convey their conventional meaning. Thus, these ligands are characterized by (a) a metal oxygen bond; and (b) the presence of a hydrocarbyl group bonded to the oxygen atom. The hydrocarbyl group may be a $C_{1-10}$ straight chained, branched or cyclic alkyl radical or a $C_{6-13}$ aromatic radical which radicals are unsubstituted or further substituted by one or more $C_{1-4}$ alkyl radicals (e.g. 2, 6 di-tertiary butyl phenoxy).

Boron heterocyclic ligands are characterized by the presence of a boron atom in a closed ring ligand (e.g. borabenzene ligands which are unsubstituted or may be substituted by one or more halogen atoms, $C_{1-10}$ alkyl group, $C_{1-10}$ alkyl group containing a hetero atom (e.g. O, or N atoms)). This definition includes heterocyclic ligands which may also contain a nitrogen atom in the ring. These ligands are well known to those skilled in the art of olefin polymerization and are fully described in the literature (see, for example, U.S. Pat. Nos. 5,637,659; 5,554,775 and the references cited therein).

The term "phosphole" is also meant to convey its conventional meaning. "Phospholes" are cyclic dienyl structures having four carbon atoms and one phosphorus atom in the closed ring. The simplest phosphole is $C_4PH_4$ (which is analogous to cyclopentadiene with one carbon in the ring being replaced by phosphorus). The phosphole ligands may be substituted with, for example, $C_{1-20}$ hydrocarbyl radicals (which may, optionally, contain halogen substituents); phosphido radicals; amido radicals; or silyl or alkoxy radicals. Phosphole ligands are also well known to those skilled in the art of olefin polymerization and are described as such in U.S. Pat. No. 5,434,116 (Sone, to Tosoh).

In the second component of the catalyst system (second catalyst) preferably L is a cyclopentadienyl-type ligand. Preferably L is a 5-membered carbon ring having delocalized bonding within the ring and bound to the metal atom through $\eta^5$ bonds and said ligand being unsubstituted or up to fully substituted with one or more substituents selected from the group consisting of $C_{1-10}$ hydrocarbyl radicals in which hydrocarbyl substituents are unsubstituted or further substituted by one or more substituents selected from the group consisting of a halogen atom and a $C_{1-8}$ alkyl radical; a halogen atom; a $C_{1-8}$ alkoxy radical; a $C_{6-10}$ aryl or aryloxy radical; an amido radical which is unsubstituted or substituted by up to two $C_{1-8}$ alkyl radicals; a phosphido radical which is unsubstituted or substituted by up to two $C_{1-8}$ alkyl radicals; silyl radicals of the formula —Si—$(R)_3$ wherein each R is independently selected from the group consisting of hydrogen, a $C_{1-8}$ alkyl or alkoxy radical, and $C_{6-10}$ aryl or aryloxy radicals; and germanyl radicals of the formula Ge—$(R)_3$ wherein R is as defined above. Most preferably the cyclopentadienyl type ligand is selected from the group consisting of a cyclopentadienyl radical, an indenyl radical and a fluorenyl radical.

The catalyst systems (e.g. first and second catalyst) in accordance with the present invention may be activated with an activator selected from the group consisting of:

(i) a complex aluminum compound of the formula $R^{12}_2AlO(R^{12}AlO)_mAlR^{12}_2$ wherein each $R^{12}$ is independently selected from the group consisting of $C_{1-20}$ hydrocarbyl radicals and m is from 3 to 50, and optionally a hindered phenol to provide a molar ratio of Al:hindered phenol from 2:1 to 5:1 if the hindered phenol is present;

(ii) ionic activators selected from the group consisting of:

(A) compounds of the formula $[R^{13}]^+ [B(R^{14})_4]^-$ wherein B is a boron atom, $R^{13}$ is a cyclic $C_{5-7}$ aromatic cation or a triphenyl methyl cation and each $R^{14}$ is independently selected from the group consisting of phenyl radicals which are unsubstituted or substituted with 3 to 5 substituents selected from the group consisting of a fluorine atom, a $C_{1-4}$ alkyl or alkoxy radical which is unsubstituted or substituted by a fluorine atom; and a silyl radical of the formula —Si—$(R^{15})_3$; wherein each $R^{15}$ is independently selected from the group consisting of a hydrogen atom and a $C_{1-4}$ alkyl radical; and (B) compounds of the formula $[(R^{18})_t ZH]^+[B(R^{14})_4]^-$ wherein B is a boron atom, H is a hydrogen atom, Z is a nitrogen atom or phosphorus atom, t is 2 or 3 and $R^{18}$ is selected from the group consisting of $C_{1-8}$ alkyl radicals, a phenyl radical which is unsubstituted or substituted by up to three $C_{1-4}$ alkyl radicals, or one $R^{18}$ taken together with the nitrogen atom may form an anilinium radical and $R^{14}$ is as defined above; and (C) compounds of the formula $B(R^{14})_3$ wherein $R^{14}$ is as defined above; and (iii) mixtures of (i) and (ii).

Preferably the activator is a complex aluminum compound of the formula $R^{12}_2AlO(R^{12}AlO)_mAlR^{12}_2$ wherein each $R^{12}$ is independently selected from the group consisting of $C_{1-20}$ hydrocarbyl radicals and m is from 3 to 50, and optionally a hindered phenol to provide a molar ratio of Al:hindered phenol from 2:1 to 5:1 if the hindered phenol is present. In the aluminum compound preferably, $R^{12}$ is methyl radical and m is from 10 to 40. The preferred molar ratio of Al:hindered phenol, if it is present, is from 3.25:1 to 4.50:1. Preferably the phenol is substituted in the 2, 4 and 6 position by a $C_{2-6}$ alkyl radical. Desirably the hindered phenol is 2,6-di-tertbutyl-4-ethyl-phenol.

The aluminum compounds (alumoxanes) are typically used in substantial molar excess compared to the amount of metal in the catalyst. Aluminum:transition metal molar ratios of from 10:1 to 10,000:1 are preferred, most preferably 10:1 to 500:1 especially from 10:1 to 50:1.

Ionic activators are well known to those skilled in the art. The "ionic activator" may abstract one activatable ligand so as to ionize the catalyst center into a cation, but not to covalently bond with the catalyst and to provide sufficient distance between the catalyst and the ionizing activator to permit a polymerizable olefin to enter the resulting active site.

Examples of ionic activators include:
triethylammonium tetra(phenyl)boron,
tripropylammonium tetra(phenyl)boron,
tri(n-butyl)ammonium tetra(phenyl)boron,
trimethylammonium tetra(p-tolyl)boron,
trimethylammonium tetra(o-tolyl)boron,
tributylammonium tetra(pentafluorophenyl)boron,
tripropylammonium tetra(o,p-dimethylphenyl)boron,
tributylammonium tetra(m,m-dimethylphenyl)boron,
tributylammonium tetra(p-trifluoromethylphenyl)boron,
tributylammonium tetra(pentafluorophenyl)boron,
tri(n-butyl)ammonium tetra(o-tolyl)boron,
N,N-dimethylanilinium tetra(phenyl)boron,
N,N-diethylanilinium tetra(phenyl)boron,
N,N-diethylanilinium tetra(phenyl)n-butylboron,
di-(isopropyl)ammonium tetra(pentafluorophenyl)boron,
dicyclohexylammonium tetra(phenyl)boron,
triphenylphosphonium tetra(phenyl)boron,
tri(methylphenyl)phosphonium tetra(phenyl)boron,
tri(dimethylphenyl)phosphonium tetra(phenyl)boron,
tropillium tetrakispentafluorophenyl borate, triphenylmethylium tetrakispentafluorophenyl borate,
tropillium phenyltrispentafluorophenyl borate,
triphenylmethylium phenyltrispentafluorophenyl borate,
benzene (diazonium) phenyltrispentafluorophenyl borate,
tropillium tetrakis (2,3,5,6-tetrafluorophenyl) borate,
triphenylmethylium tetrakis (2,3,5,6-tetrafluorophenyl) borate,
tropillium tetrakis (3,4,5-trifluorophenyl) borate,
benzene (diazonium) tetrakis (3,4,5-trifluorophenyl) borate,
tropillium tetrakis (1,2,2-trifluoroethenyl) borate,
triphenylmethylium tetrakis (1,2,2-trifluoroethenyl) borate,
tropillium tetrakis (2,3,4,5-tetrafluorophenyl) borate, and
triphenylmethylium tetrakis (2,3,4,5-tetrafluorophenyl) borate.

Readily commercially available ionic activators include:
N,N-dimethylaniliniumtetrakispentafluorophenyl borate;
triphenylmethylium tetrakispentafluorophenyl borate (tritylborate); and
trispentafluorophenyl borane.

The ionic activators may be used in amounts to provide a molar ratio of transition metal to boron that will be from 1:1 to 1:6 preferably from 1:1 to 1:2.

As noted above, the reaction mixture in a gas phase process typically comprises from 0 to 15 mole % of hydrogen, from 0 to 30 mole % of one or more $C_{3-8}$ alpha-olefins, from 15 to 100 mole % of ethylene, and from 0 to 75 mole % of one or more non reactive gases. The non reactive gas may be selected from the group consisting of nitrogen, a $C_{1-7}$ non polymerizable hydrocarbon such as an alkane (e.g. iso-pentane) or a mixture thereof.

Applicants have found in polymerizations using the catalyst of the present invention that it is possible to control the ratio of the high and low molecular weight components and the comonomer content in the high and low molecular weight fractions merely by controlling (changing) one or more of the following conditions: one or more steps selected from the group consisting of:

(a) altering the temperature of the reaction by at least 1° C., typically from 3° C. to 20° C., most preferably from 4° C. to 12° C. within the range from 50 to 120° C.;

(b) altering the partial pressure of the hydrogen component of the reaction mixture by at least 0.02 psi (0.138 KPa); typically from 0.05 to 1 psi (0.345 to 6.894 KPa);

(c) altering the partial pressure of ethylene in the reaction mixture by not less than 10 psi (69 KPa) typically from 15 to 50 psi (103.4 KPa to 344.8 KPa); and (d) altering the amount of non polymerizable hydrocarbon in the reaction mixture by not less than 0.5 mole %, typically from 1 to 20, most preferably form 3 to 12 mole %.

Generally in conventional processes the comonomer tends to be more highly incorporated in to the lower molecular weight components in the product (e.g. there are higher molecular weight components having lower comonomer incorporation). However, the process of the present invention permits the comonomer to be incorporated in a manner such that there is more comonomer in the higher molecular weight segments of the polymer (sometimes called reverse comonomer incorporation). The comonomer distribution could be a mixture of the above types. That is, the comonomer incorporation could rise (or fall) until a certain molecular weight is obtained and then it could fall (or rise) with increasing molecular weight of the polymer (resulting in a peak or a valley).

The reaction takes place in a single gas phase or slurry phase reactor. The product is removed from the reactor by conventional means and separated from diluent and/or residual monomers and further treated.

The resulting resin may typically be compounded either by the manufacturer or the converter (e.g. the company converting the resin pellets into the final product). The compounded polymer may contain fillers, pigments and other additives. Typically the fillers are inert additives such as clay, talc, $TiO_2$ and calcium carbonate which may be added to the polyolefin in amounts from 0 weight % up to about 50 weight %, preferably less than 30 weight %. The resin may contain typical amounts of antioxidants and heat and light stabilizers such as combinations of one or more of hindered phenols, phosphates, phosphites and phosphonites typically in amounts of less than 0.5 weight % based on the weight of the resin. Pigments such as carbon black may also be added to the resin in small amounts.

In the manufacture of pipe and other products, the polyethylene resin blend may contain a nucleating agent in amounts from about 1,500 to about 10,000 parts per million (ppm) based on the weight of the polyolefin. Preferably the nucleating agent is used in amounts from 2,000 to 8,000 ppm, most preferably from 2,000 to 5,000 ppm based on the weight of the polyolefin.

The nucleating agent may be selected from the group consisting of dibenzylidene sorbitol, di (p-methyl benzylidene) sorbitol, di (o-methyl benzylidene) sorbitol, di (p-ethylbenzylidene) sorbitol, bis (3,4-dimethyl benzylidene) sorbitol, bis (3,4-diethylbenzylidene) sorbitol and bis trimethylbenzylidene) sorbitol. One commercially available nucleating agent is bis (3,4-dimethyl benzylidene) sorbitol.

The polymer may be converted into sheet material such as blown or cast film (such as geomembranes), extruded articles such as pipes, rotomolded articles such as drums, tanks and sporting goods such as kayaks, blow molded articles such as bottles and small jars.

The present invention will now be illustrated by the following non-limiting examples.

EXAMPLES

Experimental

In the experiments the following abbreviations were used.

THF=tetrahydrofuran

TMS=trimethyl silyl

Molecular weight distribution and molecular weight averages (Mw, Mn, Mz) of resins were determined using high temperature Gel Permeation Chromatography (GPC) according to the ASTM D6474: "Standard Test Method for Determining Molecular Weight Distribution and Molecular Weight Averages of Polyolefins". The system was calibrated using the 16 polystyrene standards (Mw/Mn<1.1) in Mw range $5 \times 10^3$ to $8 \times 10^6$ and 3 hydrocarbon Standards $C_{60}$, $C_{40}$, and $C_{20}$.

The operating conditions are listed below:

| | |
|---|---|
| GPC instrument: | Polymer Laboratories ® 220 equipped with a refractive index detector |
| Software: | Viscotek ® DM 400 Data Manager with Trisec ® software |
| Columns: | 4 Shodex ® AT-800/S series cross-linked styrene-divinylbenzene with pore sizes $10^3$Å, $10^4$Å, $10^5$Å, $10^6$Å |
| Mobile Phase: | 1,2,4-trichlorobenzene |
| Temperature: | 140° C. |
| Flow Rate: | 1.0 ml/min |

-continued

| | |
|---|---|
| Sample Preparation: | Samples were dissolved in 1,2,4-trichloro-benzene by heating on a rotating wheel for four hours at 150° C. |
| Sample Filtration: | No |
| Sample Concentration: | 0.1% (w/v) |

The determination of branch frequency as a function of molecular weight was carried out using high temperature Gel Permeation Chromatography (GPC) and FT-IR of the eluent. Polyethylene standards with a known branch content, polystyrene and hydrocarbons with a known molecular weight were used for calibration.

Operating conditions are listed below:

| | |
|---|---|
| GPC instrument: | Waters ® 150 equipped with a refractive index detector |
| IR Instrument: | Nicolet Magna ® 750 with a Polymer Labs ® flow cell. |
| Software: | Omnic ® 5.1 FT-IR |
| Columns: | 4 Shodex ® AT-800/S series cross-linked styrene-divinylbenzene with pore sizes $10^3$Å, $10^4$Å, $10^5$Å, $10^6$Å |
| Mobile Phase: | 1,2,4-Trichlorobenzene |
| Temperature: | 140° C. |
| Flow Rate: | 1.0 ml/min |
| Sample Preparation: | Samples were dissolved in 1,2,4-trichlorobenzene by heating on a rotating wheel for five hours at 150° C. |
| Sample Filtration: | No |
| Sample Concentration: | 4 mg/g |

Synthesis of Catalyst Component 1

EtMgBr (100 mL, 3M solution in diethyl ether) was added dropwise to a solution of 4-methoxy-2-tert-butyl-phenol (290 mol) in tetrahydrofuran (THF) (350 mL) at ambient temperature to give an amber solution. After 2 hours of stirring, toluene (250 mL) was added, and the ether and THF were removed by distillation. Triethylamine (60.6 mL) and paraformaldehyde (21.8 g) were then added as a white slurry in toluene. The reaction was stirred overnight, followed by heating for 2 hours at 95° C. to give a cloudy orange solution. The resulting reaction mixture was poured into 1 M HCl while cooling to 0° C. The organic layer was separated and the aqueous phase extracted with diethyl ether. The combined organic phases were dried over $Na_2SO_4$, and then evaporated to give an oily orange material. The oil was dissolved in ethanol (250 mL) and to the clear orange solution was added cyclohexylamine (32.9 mL). The reaction was stirred for 48 hours giving a dark orange solution. The solution was cooled in a freezer causing a yellow crystalline solid to separate. The product was isolated by filtration and washed with cold ethanol. The imine product (54 mmol) was dissolved in THF (200 mL) and added dropwise to a stirring suspension of excess NaH (70 mmol) in THF (250 mL). The yellow suspension was stirred for 48 hours, the excess NaH removed by filtration and the solvent removed to give a bright yellow solid. The sodium salt (46 mmol) was dissolved in THF (150 mL) and added to a suspension of $ZrCl_4.THF_2$ (23 mmol) in THF (150 mL). The resulting yellow suspension was stirred for 48 hours. The solvent was removed giving impure product as a very sparingly soluble yellow residue. The crude material was extracted with several portions of $CH_2Cl_2$ followed by solvent removal to give a yellow solid which was washed with cold $CH_2Cl_2$/ether to remove unreacted ligand.

Synthesis of $(tBu_3PN)(n$-Butyl Indenyl$)TiCl_2$

N-BuLi (173 mmol) was added to indene (173 mmol) in THF (70 mL) at ambient temperature using an oil bath as a heat sink. The reaction was stirred for 40 minutes, then added to n-butyl bromide (223 mmol) in THF (70 mL) at 0° C. The reaction was stirred overnight at ambient temperature, followed by standard aqueous workup. Evaporation of solvent followed by distillation under reduced pressure gave pure n-butylindene. n-BuLi (13.5 mmol) was added to n-butylindene (13.5 mmol) in THF (50 mL) and stirred for 1 hour. The solution was then added to $((tBu)_3PN)TiCl_3$ (which was prepared by the reaction of $TiCl_4$ with $(tBu)_3$PN-TMS) slurried in toluene at −78° C. After stirring overnight at ambient temperature and the solvent was removed under vacuum. The residue was extracted into toluene, filtered and the filtrate concentrated. Addition of heptane precipitated the product that was isolated by filtration.

Synthesis of $(tBu_3PN)(C_6F_5CH_2Cp)TiCl_2$

N-BuLi (60 mmol) was added to a solution of trimethylsilylcyclopentadiene, TMS-$C_5H_5$ (60 mmol) in THF (40 mL). After 30 minutes, the solution was added to pentafluorobenzylbromide (60 mmol) in THF at −45° C. The reaction was stirred for 2 hours and the solvent removed under vacuum. The crude residue was distilled under reduced pressure until it was mostly free of unreacted TMSCpH. The $(TMS)(C_6F_5CH_2)C_5H_4$ (22.8 mmol) was added to $TiCl_4$ (27 mmol) dropwise over a period of 30 minutes. Toluene was added to ensure continued stirring. Repeated trituration with heptane gave the desired product as a solid that could be isolated by filtration.

Synthesis of $(tBu_3PN)(n$-$BuCpC_6F_5)TiCl_2$

Sodium cyclopentadiene (615 mmol) was dissolved in tetrahydrofuran and a solution of perfluorobenzene (309 mmol) was added as a 1:1 solution with THF over a 20 minute period. The resulting mixture was for 3 hours at 60° C., allowed to cool, then added by cannula transfer to neat chlorotrimethylsilane (60 mL) at 0° C. over 15 minutes. The reaction was allowed to warm to ambient temperature for 30 minutes, followed by slow concentration over a 3 hour period to remove excess chlorotrimethylsilane and solvents. The resulting wet solid was slurried in heptane and filtered. Concentration of the heptane filtrate gave crude (TMS) $(C_6F_5)C_5H_4$ as a brown oil which was used without further purification. $(TMS)(C_6F_5)C_5H_4$ (50 mmol) was dissolved in THF and cooled to 0° C. The solution was treated with n-BuLi (50 mmol), which was added dropwise. After stirring for 10 minutes at 0° C., the reaction was allowed to warm to ambient temperature and stirred for a further 1 hour. A cold solution of n-butyl bromide (50 mmol) was prepared in THF (35 mL), and to this was added the $[(TMS)(C_6F_5)C_5H_3]Li$ solution. The resulting mixture was stirred for 2 hours and the THF was removed by evaporation under vacuum. The residue was extracted into heptane (150 mL), filtered and the solvent was evaporated. $TiCl_4$ (60 mmol) was added to the (n-Bu)(TMS)$(C_6F_5)C_5H_3$ via pipette and the solution was heated to 60° C. for 3 hours. Removal of excess $TiCl_4$ under vacuum gave a thick oil. Addition of pentane caused immediate precipitation of product $((nBu)(C_6F_5) C_5H_3)TiCl_3$ which was isolated by filtration. ((nBu)(C$_6$F$_5$)C$_5$H$_3$)TiCl$_3$ (15.6 mmol) was mixed with (tBu)$_3$PN-TMS (15.6 mmol) in toluene and stirred overnight at ambient temperature. The solution was filtered and the solvent removed to give desired product.

Preparation of Silica-Supported Aluminoxane (MAO)

Sylopol XPO-2408 silica purchased from Grace Davison was calcined by fluidizing with air at 200° C. for 2 hours and subsequently with nitrogen at 600° C. for 6 hours. 44.6 grams of the calcined silica was added in 100 mL of toluene. 150.7 g of a MAO solution containing 4.5 weight % Al purchased from Albemarle was added to the silica slurry. The mixture was stirred for 1 hour at ambient temperature. The solvent was removed by vacuum, yielding a free flowing solid containing 11.5 weight % Al.

Example 1

Preparation of Catalyst A

In a glovebox, 1.95 g of silica-supported MAO prepared above was slurried in 15 mL of toluene. Separately, 35 mg of catalyst component 1 was dissolved in 20 mL of toluene, and 12 mg of (tBu$_3$PN)(n-butyl indenyl)TiCl$_2$ was dissolved in 20 mL of toluene. Both catalyst solutions were added simultaneously to the silica slurry. After 1 hour of stirring, the slurry was filtered, yielding a clear filtrate. The solid component was washed twice with toluene, and once with heptane. The final product was dried in vacuo to 300 mtorr (40 Pa) and stored under nitrogen until use.

Polymerization

A 2 L stirred autoclave reactor was heated at 100° C. for 1 hour and thoroughly purged with nitrogen. 160 g of NaCl predried in an oven at 160° C. for at least a week was added in the reactor which was subsequently pressure purged three times with nitrogen and twice with ethylene at 100° C. The reactor was then cooled to 90° C. and an aliquot of 25 weight % triisobutyl aluminum (TiBAL) was added. The amount of TiBAL was such that the molar ratio of TiBAL to the total transition metal in the catalyst to be added was around 500:1. 2 mL of purified 1-hexene was then added and the reactor was pressurized with 100 psig of ethylene. 200 psig of ethylene was used to push 19.2 mg of Catalyst A from a catalyst tubing into the reactor to start the reaction. During the polymerization, the reactor pressure was maintained constant with 200 psig of ethylene and 1-hexene was continuously fed into the reactor as 10 weight % of ethylene feeding rate using a mass flow controller. The polymerization was carried out at 90° C. for 1 hour, yielding 20.0 g of polymer.

FIG. 1 shows the GPC-FTIR plot of the polymer. The profile shows a clear bimodality with most of the comonomer incorporation being in the high molecular weight fraction.

Example 2

Preparation of Catalyst B

In a glovebox, 1.95 grams of silica-supported MAO prepared above was slurried in 15 mL of toluene. Separately, 26 mg of catalyst component 1 was dissolved in 20 mL of toluene, and 21 mg of (tBu$_3$PN)(C$_6$F$_5$CH$_2$ Cp)TiCl$_2$ was dissolved in 20 mL of toluene. Both catalyst solutions were added simultaneously to the silica slurry. After one hour of stirring, the slurry was filtered, yielding a clear filtrate. The solid component was washed twice with toluene, and once with heptane. The final product was dried in vacuo to 300 mTorr and stored under nitrogen until use.

Polymerization

The polymerization was the same as Example 1, except that 26.7 mg of Catalyst B was used for polymerization, producing 46.8 g of polymer.

Figure 2:
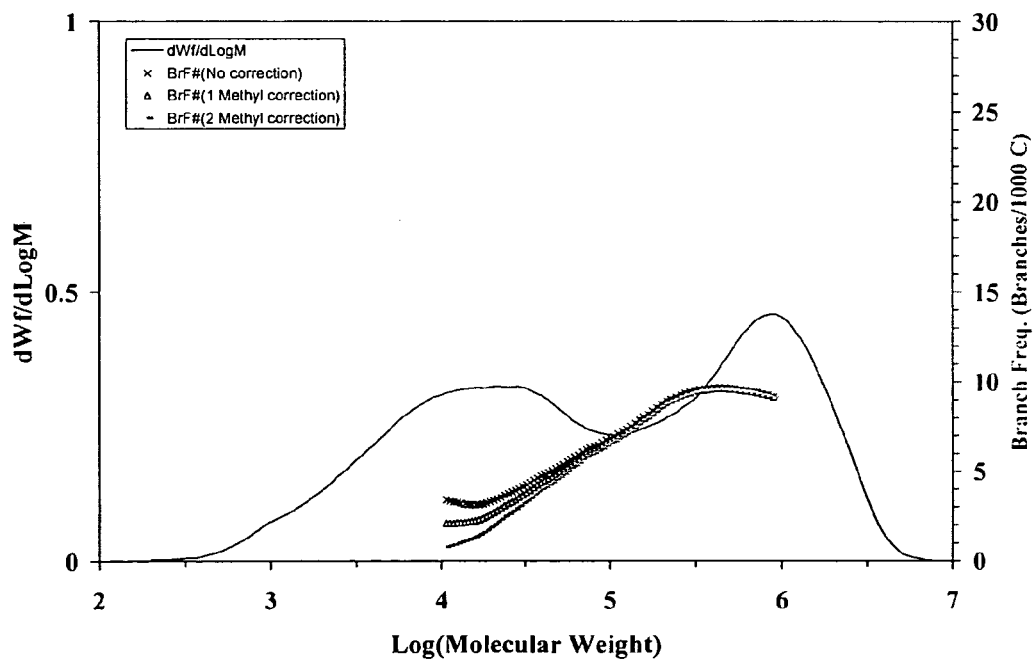
FIG. 2 is a GPC-FTIR profile of the resin produced in Example 2.

As seen in FIG. 2, the GPC-FTIR plot shows that the polymer is bimodal with most of comonomer incorporation in the high molecular weight fraction.

Example 3

Preparation of Catalyst C

In a glovebox, 2.92 grams of silica-supported MAO prepared above was slurried in 30 mL of toluene. Separately, 63.0 mg of catalyst component 1 was dissolved in 25 mL of toluene, and 13.3 mg of (tBU$_3$PN)(C$_6$F$_5$)(n-Bu)CpTiCl$_2$ was dissolved in 10 mL of toluene. Both catalyst solutions were added simultaneously to the silica slurry. After one hour of stirring, the slurry was filtered, yielding a clear filtrate. The solid component was washed twice with toluene, and once with heptane. The final product was dried in vacuo to 300 mTorr (40 10$^2$ Pa) and stored under nitrogen until use.

Polymerization

The polymerization was the same as Example 1, except that 20.9 mg of Catalyst C was used for polymerization, producing 45.8 g of polymer Example 4

Preparation of Catalyst D

Catalyst D was prepared in the same manner as Catalyst C, except that the molar ratio of catalyst component 1 to (tBu$_3$PN)(C$_6$F$_5$)(n-Bu)CpTiCl$_2$ was 1:1 M/M. The loading of catalyst components on silica was 0.0355 mmol/g of catalyst.

Polymerization

The polymerization was the same as Example 3, except that 19.6 mg of Catalyst D was used for polymerization, producing 17.8 g of polymer.

Example 5

Preparation of Catalyst E

Catalyst E was prepared in the same manner as Catalyst C, except that the molar ratio of catalyst component 1 to (Bu$_3$PN)(C$_6$F$_5$)(n-Bu)CpTiCl$_2$ was 1:2 M/M. The loading of catalyst components on silica was 0.0355 mmol/g of catalyst.

Polymerization

The polymerization was the same as Example 3, except that 20.7 mg of Catalyst E was used for polymerization, producing 38.0 g of polymer.

Figure 3:
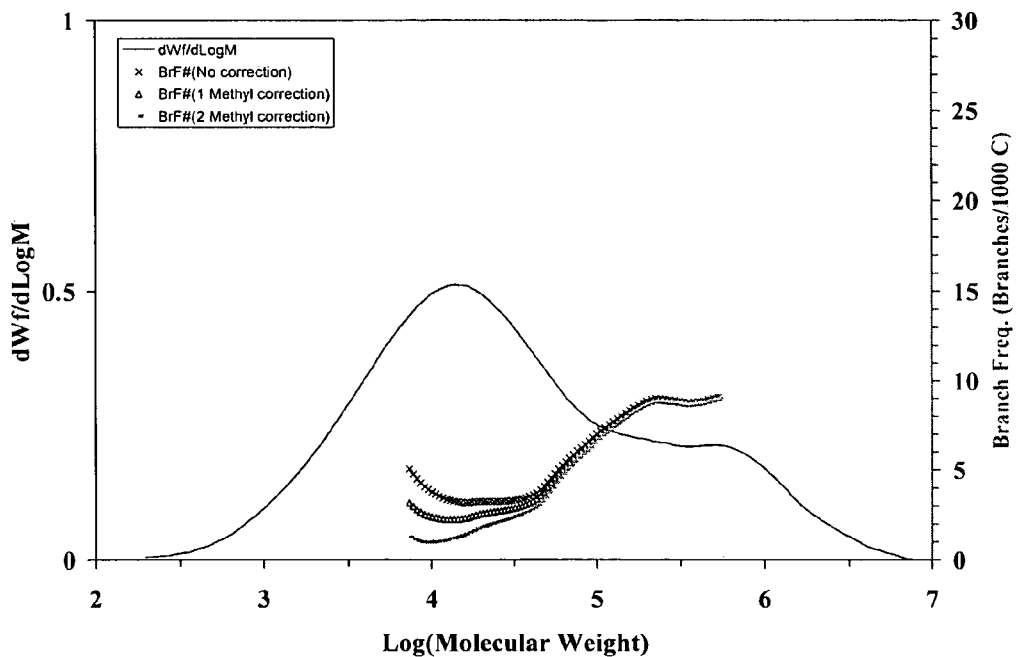
FIG. 3 is a GPC-FTIR profile of the resin produced in Example 3.
Figure 4:
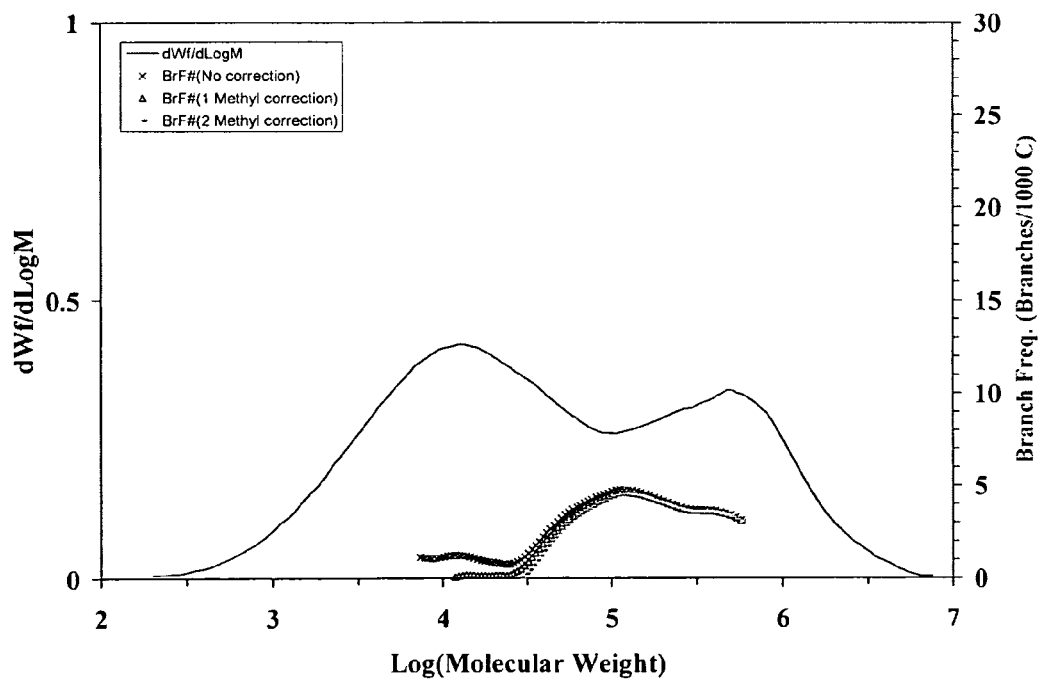
FIG. 4 is a GPC-FTIR profile of the resin produced in Example 4.
Figure 5:
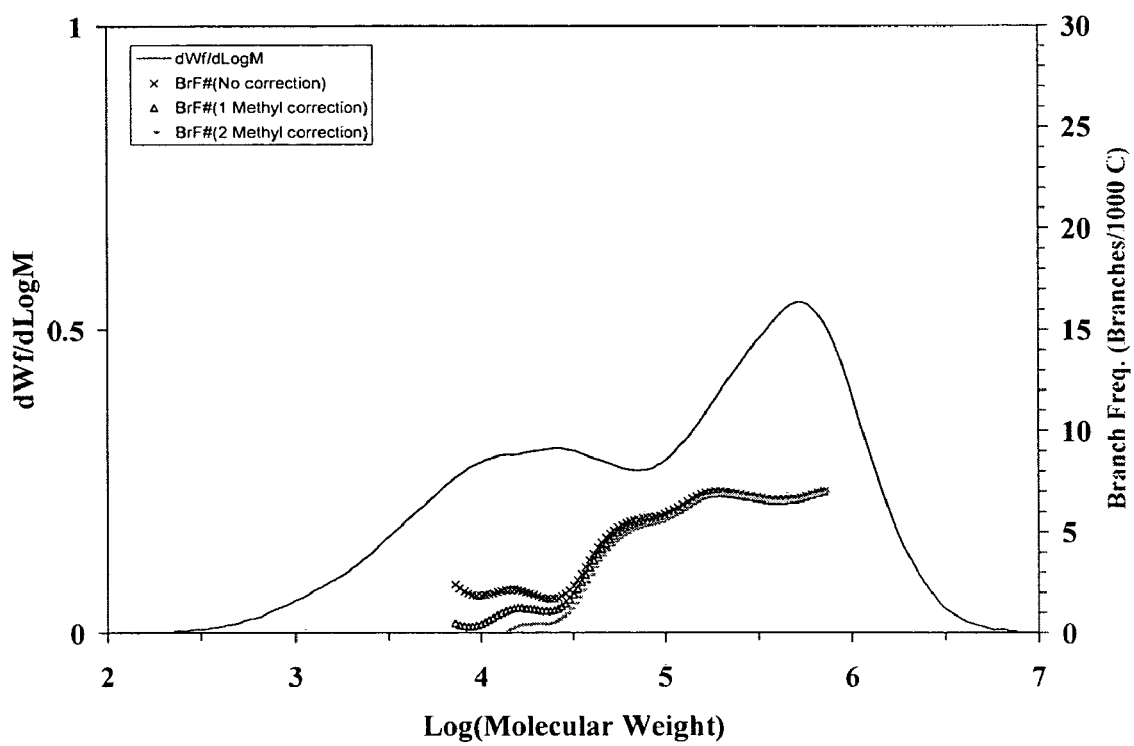
FIG. 5 is a GPC-FTIR profile of the resin produced in Example 5.

The GPC-FTIR profiles of the resins produced in Examples 3–5 are shown in FIGS. 3–5, respectively. In all of these examples, bimodal resins with high comonomer contents in the high molecular fraction are produced. As the molar ratio of (tBu₃PN)(C₆F₅CH₂ Cp)TiCl₂ to catalyst component 1 increases (from Example 3 to 5), the ratio of the high MW fraction to the low MW fraction increases and the Mw of the bimodal resins also increases steadily (Table 1). This implies that the composition of the bimodal resins is readily controlled by the ratio of the two catalyst components in the supported catalyst.

TABLE 1

Effect of Component Ratio on Supported (tBu₃PN)(C₆F₅)(n-Bu)CpTiCl₂/Catalyst Component 1

| Example | (tBu₃PN)(C₆F₅)(n-Bu)CpTiCl₂/Catalyst Component 1 (M/M) | Productivity (g/g) | Mn (×10³) | Mw (×10³) |
|---|---|---|---|---|
| 3 | 1:4 | 2,191 | 9.38 | 97.5 |
| 4 | 1:2 | 908 | 10.90 | 127.4 |
| 5 | 1:1 | 1,836 | 15.80 | 192.4 |

What is claimed is:

1. A dual catalyst system suitable for producing a bimodal resin having at least one higher molecular weight fraction having a greater comonomer incorporation than that of a lower molecular weight fraction wherein:
   (i) the first component of which comprises a compound of the formula:

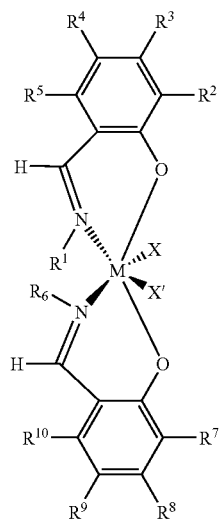

wherein M is a group IV transition metal; R¹ and R⁶ are independently selected from the group consisting of a hydrogen atom, alkyl radicals having up to 15 carbon atoms, aryl radicals having up to 25 carbon atoms, alkoxy radicals having up to 15 carbon atoms, and amido radicals which are unsubstituted or substituted by up to two alkyl radicals containing up to 15 carbon atoms, R² and R⁷ are independently selected from the group consisting of alkyl radicals having up to 15 carbon atoms, aryl radicals having up to 25 carbon atoms and silyl radicals of the formula Si(R¹¹)₃ wherein each R¹¹ is independently selected from the group consisting of alkyl radicals having up to 15, carbon atoms, and aryl radicals having up to 25 carbon atoms; R³, R⁴, R⁵, R⁸, R⁹ and R¹⁰ are independently selected from the group consisting of a hydrogen atom, a heteroatom containing group having up to 20 carbon atoms, and a hydrocarbon group containing up to 25 carbon atoms, provided that none of these groups has a Hammett σ_p value greater than 0.20; X and X' are selected from the group consisting of a halogen atom, alkyl radicals having up to 15 carbon atoms, aryl radicals having up to 25 carbon atoms, alkoxy radicals having up to 15 carbon atoms, amido radicals which are unsubstituted or substituted by up to two alkyl radicals containing up to 15 carbon atoms, and phenoxy radicals having up to 18 carbon atoms;
   (ii) the second component of which comprises a compound of the formula:

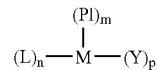

wherein M is a group 4 metal; Pl is a phosphinimine ligand; L is a monoanionic ligand selected from the group consisting of a cyclopentadienyl-type ligand or a bulky heteroatom ligand; Y is an activatable ligand; m is 1 or 2; n is 0 or 1; and p is an integer and the sum of m+n+p equals the valence state of M.

2. The dual catalyst system according to claim 1, wherein the molar ratio of the first component to the second component is from 80:20 to 20:80.

3. The catalyst according to claim 2, further including an activator selected from the group consisting of:
   (i) a complex aluminum compound of the formula R¹²₂AlO(R¹²AlO)_mAlR¹²₂ wherein each R¹² is independently selected from the group consisting of C₁₋₂₀ hydrocarbyl radicals and m is from 3 to 50, and optionally a hindered phenol to provide a molar ratio of Al:hindered phenol from 2:1 to 5:1 if the hindered phenol is present;
   (ii) ionic activators selected from the group consisting of:
      (A) compounds of the formula [R¹³]⁺ [B(R¹⁴)₄]⁻ wherein B is a boron atom, R¹³ is a cyclic C₅₋₇ aromatic cation or a triphenyl methyl cation and each R¹⁴ is independently selected from the group consisting of phenyl radicals which are unsubstituted or substituted with 3 to 5 substituents selected from the group consisting of a fluorine atom, a C₁₋₄ alkyl or alkoxy radical which is unsubstituted or substituted by a fluorine atom; and a silyl radical of the formula —Si—(R¹⁵)₃; wherein each R¹⁵ is independently selected from the group consisting of a hydrogen atom and a C₁₋₄ alkyl radical; and
      (B) compounds of the formula [(R¹⁸)_t ZH]⁺[B(R¹⁴)₄]⁻ wherein B is a boron atom, H is a hydrogen atom, Z is a nitrogen atom or phosphorus atom, t is 2 or 3 and R¹⁸ is selected from the group consisting of C₁₋₈ alkyl radicals, a phenyl radical which is unsubstituted or substituted by up to three C₁₋₄ alkyl radicals, or one R¹⁸ taken together with the nitrogen atom may form an anilinium radical and R¹⁴ is as defined above; and (C) compounds of the formula $B(R^{14})_3$ wherein $R^{14}$ is as defined above; and (iii) mixtures of (i) and (ii).

4. The dual catalyst system according to claim 3, wherein both the first and second catalyst components are supported on the same support.

5. The dual catalyst system according to claim 4, wherein the support is an inorganic support or organic support.

6. The dual catalyst system according to claim 5, wherein the support is silica.

7. The dual catalyst system according to claim 6, wherein the support has an average particle size from about 10 to 150 microns, a surface area greater than 100 $m^2/g$, and a pore volume from about 0.3 to 5.0 ml/g.

8. The dual catalyst according to claim 7, wherein in the second component L is a cyclopentadienyl type ligand selected from the group consisting of a $C_{5-13}$ ligand containing a 5-membered carbon ring having delocalized bonding within the ring and bound to the metal atom through $\eta^5$ bonds and said ligand being unsubstituted or up to fully substituted with one or more substituents selected from the group consisting of $C_{1-10}$ hydrocarbyl radicals in which hydrocarbyl substituents are unsubstituted or further substituted by one or more substituents selected from the group consisting of a halogen atom and a $C_{1-8}$ alkyl radical; a halogen atom; a $C_{1-8}$ alkoxy radical; a $C_{6-10}$ aryl or aryloxy radical; an amido radical which is unsubstituted or substituted by up to two $C_{1-8}$ alkyl radicals; a phosphido radical which is unsubstituted or substituted by up to two $C_{1-8}$ alkyl radicals; silyl radicals of the formula —Si—$(R)_3$ wherein each R is independently selected from the group consisting of hydrogen, a $C_{1-8}$ alkyl or alkoxy radical, and $C_{6-10}$ aryl or aryloxy radicals; and germanyl radicals of the formula Ge—$(R)_3$ wherein R is as defined above.

9. The dual catalyst system according to claim 8, wherein in the second component Y is selected from the group consisting of a hydrogen atom; a halogen atom, a $C_{1-10}$ hydrocarbyl radical; a $C_{1-10}$ alkoxy radical; a $C_{5-10}$ aryl oxide radical; each of which said hydrocarbyl, alkoxy, and aryl oxide radicals may be unsubstituted by or further substituted by one or more substituents selected from the group consisting of a halogen atom; a $C_{1-8}$ alkyl radical; a $C_{1-8}$ alkoxy radical; a $C_{6-10}$ aryl or aryloxy radical; an amido radical which is unsubstituted or substituted by up to two $C_{1-8}$ alkyl radicals.

10. The dual catalyst system according to claim 9, wherein in the second component the phosphinimine ligand has the formula $((R^{21})_3P=N—$ wherein each $R^{21}$ is independently selected from the group consisting of $C_{1-6}$ alkyl radicals.

11. The dual catalyst system according to claim 10, wherein in the second component Cp is selected from the group consisting of a cyclopentadienyl radical, an indenyl radical and a fluorenyl radical.

12. The dual catalyst system according to claim 11, wherein in the second component Y is selected from the group consisting of a hydrogen atom, a chlorine atom and a $C_{1-4}$ alkyl radical.

13. The dual catalyst system according to claim 12, wherein in the second component the phosphinimine ligand is tris t-butyl phosphinimine.

14. The dual catalyst according to claim 13, wherein the activator is a complex aluminum compound wherein $R^{12}$ is a methyl radical and m is from 10 to 40.

15. The dual catalyst system according to claim 14, wherein the molar ratio of Al to transition metal is from 10:1 to 500:1.

16. The dual catalyst system according to claim 15, wherein the activator is a mixture of a complex aluminum compound and a hindered phenol.

17. The dual catalyst system according to claim 16, wherein the molar ratio of Al:hindered phenol is from 3.25:1 to 4.50:1.

18. The dual catalyst system according to claim 17, wherein the hindered phenol is 2,6-di-t-butyl-4-ethyl phenol.

19. The dual catalyst system according to claim 13, wherein the activator is an ionic activator.

20. The dual catalyst system according to claim 19, wherein the molar ratio of transition metal to boron is from 1:1 to 1:3.

21. The dual catalyst system according to claim 20, wherein ionic activator is a tritylborate.

22. The dual catalyst system according to claim 20, wherein the molar ratio of transition metal to boron is from 1:1.05 to 1:1.20.

23. The dual catalyst system according to claim 13, wherein the activator is a mixture of an aluminum compound together with a hindered phenol and an ionic activator to provide a molar ratio of transition metal:Al:boron from 1:20:1 to 1:120:3.

24. The dual catalyst system according to claim 23, wherein the molar ratio of Al:hindered phenol is from 3.25:1 to 4.50:1.

25. The dual catalyst system according to claim 24, wherein the catalyst system has a molar ratio of transition metal:Al:boron from 1:30:1 to 1:45:1.5.

26. The dual catalyst system according to claim 25, wherein the ionic activator is a tritylborate.

27. The dual catalyst system according to claim 26, wherein the hindered phenol is 2,6-di-t-butyl-4-ethyl phenol.

* * * * *

UNITED STATES PATENT AND TRADEMARK OFFICE
CERTIFICATE OF CORRECTION

PATENT NO. : 7,064,096 B2
APPLICATION NO. : 11/006436
DATED : June 20, 2006
INVENTOR(S) : Peter Phung Minh Hoang et al.

It is certified that error appears in the above-identified patent and that said Letters Patent is hereby corrected as shown below:

In example 3, col. 16, line 27 reads "tBU", but should read -- tBu --.

In example 4, col. 16, line 48 reads "1:1", but should read -- 2:1 --.

In example 5, col. 16, line 65, reads "1:2", but should read -- 1:1 --.

Signed and Sealed this

Eleventh Day of December, 2007

JON W. DUDAS
*Director of the United States Patent and Trademark Office*